(12) United States Patent
Fouache

(10) Patent No.: US 9,766,161 B2
(45) Date of Patent: Sep. 19, 2017

(54) SYSTEM DEDICATED TO MONITORING THE PHYSICAL AND/OR ANALOGUE PARAMETERS OF THE PARTS OF AN ENGINE

(71) Applicant: CONTROLE MESURE REGULATION, Marseilles (FR)

(72) Inventor: Pascal Fouache, Meyreuil (FR)

(73) Assignee: CONTROLE MESURE REGULATION, Marseilles (FR)

( * ) Notice: Subject to any disclaimer, the term of this patent is extended or adjusted under 35 U.S.C. 154(b) by 185 days.

(21) Appl. No.: 14/434,432

(22) PCT Filed: Oct. 9, 2013

(86) PCT No.: PCT/FR2013/052409
§ 371 (c)(1),
(2) Date: Apr. 9, 2015

(87) PCT Pub. No.: WO2014/057219
PCT Pub. Date: Apr. 17, 2014

(65) Prior Publication Data
US 2015/0241305 A1   Aug. 27, 2015

(30) Foreign Application Priority Data
Oct. 10, 2012 (FR) ...................... 12 02706

(51) Int. Cl.
*G01M 15/05* (2006.01)
*H04Q 9/00* (2006.01)
(Continued)

(52) U.S. Cl.
CPC ........... *G01M 15/05* (2013.01); *G01K 11/265* (2013.01); *G01N 29/2481* (2013.01); *H04Q 9/00* (2013.01); *G01K 2205/00* (2013.01)

(58) Field of Classification Search
CPC .................. G01M 15/05; G01K 11/265; G01K 2205/00; G01N 29/2481; H04Q 9/00
(Continued)

(56) References Cited

U.S. PATENT DOCUMENTS

| 6,239,723 | B1 | 5/2001 | Bauerschmidt et al. |
| 7,911,324 | B2 * | 3/2011 | Breed .................... G01S 13/878 307/10.1 |
| 2006/0025897 | A1 * | 2/2006 | Shostak ................ B60C 23/005 701/1 |

FOREIGN PATENT DOCUMENTS

| DE | 103 25 667 | 3/2005 |
| EP | 0.051.035 | 5/1982 |

(Continued)

*Primary Examiner* — Mahmoud Gimie
(74) *Attorney, Agent, or Firm* — Pearl Cohen Zedek Latzer Baratz LLP

(57) ABSTRACT

The invention concerns a system for monitoring physical and/or analogue parameters relative to the parts of an engine, said system comprising at least one electronic control unit ($30_a$) configured to call up data, via at least one antenna ($20a$), from a surface acoustic wave sensor located on one of said parts, characterised by the fact that:—the engine (M) is compartmentalized, each compartment (Ma, . . . , Mf) comprising a plurality of mobile or fixed parts of which the physical and/or analogue parameters need to be monitored, —each of these parts to be monitored is provided with a surface acoustic wave sensor ($101a$, $102a$, $103a$, . . . , $101f$, $102f$, $103f$), each of said sensors having a distinct resonance frequency specific to it,—an antenna ($20a$, . . . , $20f$) is installed inside each of the compartments (Ma, . . . , Mf), each of said antenna being connected, alone or in pairs, to an electronic control unit ($30a$, . . . , $30f$, $30ab$, . . . , $30ef$),— each antenna ($20a$, . . . , $20f$) is controlled by the electronic control unit ($30a$, . . . , $30f$, $30ab$, . . . , $30ef$) to which it is connected, to simultaneously emit a plurality of distinct
(Continued)

frequencies close to the resonance frequencies of the sensors (101*a*, 102*a*, 103*a*, ..., 101*f*, 102*f*, 103*f*) which are located in the engine compartment (Ma, ..., Mf) of said antenna, so as to simultaneously communicate with all of these sensors (101*a*, 102*a*, 103*a*, ..., 101*f*, 102*f*, 103*f*).

18 Claims, 5 Drawing Sheets

(51) Int. Cl.
  *G01K 11/26* (2006.01)
  *G01N 29/24* (2006.01)
(58) Field of Classification Search
  USPC .......................................................... 701/101
  See application file for complete search history.

(56) References Cited

FOREIGN PATENT DOCUMENTS

| | | |
|---|---|---|
| EP | 2.422.900 | 2/2012 |
| WO | WO 97/28589 | 8/1997 |
| WO | WO 00/62029 | 10/2000 |

\* cited by examiner

SYSTEM DEDICATED TO MONITORING THE PHYSICAL AND/OR ANALOGUE PARAMETERS OF THE PARTS OF AN ENGINE

CROSS-REFERENCE TO RELATED APPLICATIONS

This application is a National Phase Application of PCT International Application No. PCT/FR2013/052409, entitled "SYSTEM DEDICATED TO MONITORING THE PHYSICAL AND/OR ANALOGUE PARAMETERS OF THE PARTS OF AN ENGINE", International Filing Date Oct. 9, 2013, published on Apr. 17, 2014 as International Publication No. WO 2014/057219, which in turn claims priority from French Patent Application No. 1202706, filed Oct. 10, 2012, all of which are incorporated herein by reference in their entirety.

TECHNICAL FIELD OF THE INVENTION

The invention has for object a system dedicated to monitoring the physical and/or analog parameters of the parts of an engine.

The invention relates to the techniques for measuring and controlling varied parameters on mobile and/or inaccessible mechanical parts of an engine, intended in particular for the monitoring and the safety of reciprocating internal combustion engines.

BACKGROUND

It is essential to provide for the control of parameters that are significant for the integrity and proper operation of the members and components of the engine. For this, the usual method consists in taking measurements directly on these components. In the event of an abnormal variation of a factor such as temperature, pressure or stress, it is then possible to stop the system before an incident occurs and the engine ceases to operate. This is for example the case when a part is insufficiently lubricated or subjected to an excessively high temperature. According to the use that is made of the equipment, the sanitary or economic consequences can be very substantial. Allowing for an anticipated and automatic stopping of the system if an abnormal parameter is observed is a major advantage. The effectiveness of such a device is therefore to a large extent dependent on its rapidity.

Prior art describes several systems that make it possible to carry out such a control.

For example, patent document EP 0.051.035 (CMR) discloses a device for controlling the temperature of the internal mobile parts of an engine by the intermediary of a transmitter-receiver formed of two fixed coils. This transmitter-receiver emits a signal carried by a magnetic circuit resonating at a determined frequency. This signal is detected by a sensor (formed by one mobile coil) placed on a moving part, and connected to a thermistor that reacts to the temperature of the part by influencing the sensitivity of said sensor, which therefore detects more or less substantially the signal that is sent to it by the transmitter-receiver. The resonating signal is measured by the transmitter-receiver and is interpreted by an electronic device as a temperature unit.

In this device, several restricting aspects are to be noted. First of all, it is the thermistor that defines the response of the sensor according to non-linear variations, which is inconvenient since according to the quality and the precision of this element, the measurements can be distorted over wide ranges of variation. In addition, the transmitter-receiver generates a magnetic field through which the waves travel. However, this magnetic field is not entirely detected by the sensor, which results in the loss of a portion of the waves emitted and received by the transmitter/receiver. The precision of the measurement therefore depends on the quality of the coil of the system and on the meticulous calibrations to be carried out for each sensor in the factory. Then, the maximum reading distance that separates the transmitter/receiver from the sensor is only of a magnitude of 2 mm, which is rather low and can cause a problem for certain moving parts, for example in relation to the operating clearances that can be of the same order of magnitude. These problems do not make it possible to respond satisfactorily to user expectations.

Patent document WO 00/62029 (SENSIT) also discloses a system based on the use of filters of surface acoustic waves (or SAW) which consists in emitting electromagnetic waves via a stationary antenna, which are converted into mechanical waves in a device constituted of piezoelectric crystal or ceramic. This wave is diluted as it propagates through the component before it is reconverted into an electrical signal by electrodes. This response signal is reconfigured to produce a finite analog impulse response through a filter. This method is based on the principle of delay lines. The delay of the reflected wave depends on the temperature. In this system which is shown in FIG. 1, a single electronic control unit 3 calls up, via antennas 2, several SAW sensors 1 placed in each engine compartment, on the parts for which the temperature must be measured. The information is communicated by the electronic control unit 3 to monitoring equipment 6 via a digital bus 5.

This system has several disadvantages. Firstly, this is a system that calls up each SAW sensor 1 via a single and same electronic control unit 3. For this, it uses the multiplexing of antennas 2, a method making it possible to call up each sensor 1 sequentially. However, this method is restrictive since it substantially increases the waiting time between each operation of calling up sensors 1. Indeed, in this system, the single control unit 3 successively calls up the sensors 1 by first sending a signal via coaxial cables 4 connected to the antennas 2. The latter communicate with the SAW sensors 1. The response signal follows the reverse path. The reception and the processing of the multiple signals received by the electronic control unit 3 increase the duration of the analysis. In addition, the metal environment of the engine has for effect to result in the loss of a portion of these signals and therefore to reduce the effectiveness of the measurements taken. Furthermore, the process for calling up SAW sensors 1 requires that each one have an antenna 2 which is dedicated to it in the engine compartment. Each communication between the antenna 2 and its SAW sensor 1 is carried out by the intermediary of a single and same frequency for all of the antennas 2. Using this single frequency therefore imposes sequential calling up of each sensor 1 in order to prevent the interferences between the responses of nearby sensors.

One of the advantages of this system in relation to other known systems of prior art, is the greater reading distance of the SAW sensors 1 by the antennas 2, said distance is increased up to 5 cm. But this distance still remains insufficient to relieve the user from the installation constraints inside the engine. Moreover, the system requires that the control unit 3 be connected to the antennas 2 by as many coaxial cables 4 and therefore imposes space constraints and very awkward cabling outside the engine.

Patent documents EP 2.422.900 (SMS CONCAST) and U.S. Pat. No. 6,239,723 (SIEMENS) disclose systems that make it possible to call up SAW sensors, arranged respectively in a mold and in an electrical cabinet. These SAW sensors are arranged on parts that are fixed, non-mobile and easy to access, and in an environment that is much less restrictive than that of an engine.

SUMMARY

In light of this situation, the main objective of the invention is to overcome the aforementioned disadvantages, and in particular to improve the capacities of measuring mobile parts that are difficult to access.

Another objective of the invention is to obtain an analysis that is faster and more precise that those obtained with the systems of prior art, avoiding the constraints imposed by the method of multiplexing disclosed in the aforementioned patent document WO 00/62029 (SENSIT).

The invention also has for objective to propose a system for monitoring that makes it possible to reduce the space and cabling constraints in relation to those imposed in the system of the aforementioned patent document WO 00/62029 (SENSIT).

The invention further has for objective to improve the performance with regards to the problems linked to the metal environment of the housing of the engine.

The solution proposed by the invention is a system for monitoring physical and/or analog parameters concerning the parts of an engine, said system comprising at least one electronic control unit configured to call up, by the intermediary of at least one antenna, a surface acoustic wave sensor (or SAW sensor) located on one of said parts.

This system is remarkable in that:
  the engine is compartmentalized, each compartment comprising several mobile parts of which the physical and/or analog parameters need to be monitored,
  each of these parts to be monitored is provided with a surface acoustic wave sensor, these sensors each having a distinct resonance frequency specific to them,
  an antenna is installed inside each of the compartments, with each of these antennas being connected, alone or in pairs, to an electronic control unit,
  each antenna is controlled by the electronic control unit to which it is connected, to simultaneously emit a plurality of distinct frequencies close to the resonance frequencies of the sensors which are located in the engine compartment of said antenna, so as to simultaneously communicate with all of these sensors.

In each compartment, a single antenna is now able to simultaneously call up all of the sensors that are installed therein. The measuring capacities are therefore not only increased tenfold, but the analysis of the parameters becomes faster and more precise than those obtained with the systems of prior art in particular that described in the aforementioned patent document WO 00/62029 (SENSIT).

Other characteristics of the invention are listed hereinbelow, with each one of these characteristics able to be considered individually or in combination with the remarkable characteristics defined hereinabove:
  The antenna that is installed in one compartment can emit frequencies in a predefined frequency band which is different from the frequency band in which emits the antenna arranged in another compartment.
  The surface acoustic wave sensors arranged in the same compartment can emit in return frequencies in a frequency band different from those emitted in return by the surface acoustic wave sensors arranged in another neighboring compartment.
  The surface acoustic wave sensors arranged in the same compartment can each emit frequencies in a narrow frequency band, defined over an interval of 2 MHz.
  Each electronic control unit can be connected to a single antenna specific to it or connected to two antennas, with each one of these antennas being installed inside a compartment that is devoted to it.
  Each surface acoustic wave sensor comprises advantageously an antenna specific to it.
  Each surface acoustic wave sensor is preferentially installed on a part which is mobile but can be installed on a part which is fixed.
  The sensors are preferentially arranged in the various compartments in such a way that sensors located in one compartment cannot communicate with an antenna installed in another compartment.
  The electronic control units can each be installed outside or inside the compartment.
  The electronic control units can be connected together by digital communication cables, at least one of said units being connected to monitoring equipment in such a way that all of said units can communicate with said equipment.
  The electronic control units can communicate with monitoring equipment by the intermediary of a digital bus.
  Each antenna can use ISM frequencies to communicate with the sensors that are associated to them.
  Each antenna can use ISM frequencies between 433 MHz and 445 MHz or ISM frequencies between 866 MHz and 890 MHz.
  Each antenna can use frequencies between 423 MHz and 435 MHz, or frequencies between 846 MHz and 870 MHz, to communicate with the sensors that are associated to them.
  Each antenna used is advantageously a "¼ wave" antenna or PIFA.

Another aspect of the invention relates to a method for monitoring physical and/or analog parameters concerning the parts of an engine, by calling up, by the intermediary of at least one antenna a surface acoustic wave sensor located on one of said parts. This method is remarkable in that it comprises the following steps:
  compartmentalizing the engine in such a way that each compartment comprises several parts of which the physical and/or analog parameters need to be monitored,
  arranging on each of these parts to be monitored, a surface acoustic wave sensor, these sensors each having a distinct resonance frequency specific to them,
  installing an antenna inside each compartment,
  connecting each one of these antennas, alone or in pairs, to an electronic control unit,
  calling up each sensor by simultaneously emitting, from each antenna, several distinct frequencies close to the resonance frequencies of the sensors which are located in the engine compartment of said antenna, so as to simultaneously communicate with all of these sensors.

DESCRIPTION OF THE FIGURES

Other advantages and characteristics of the inventions shall appear more clearly when reading the following description of a preferred embodiment, in reference to the annexed drawings, provided by way of indicative and non-restricted examples and wherein.

aforementioned

DETAILED DESCRIPTION

Figure 1:
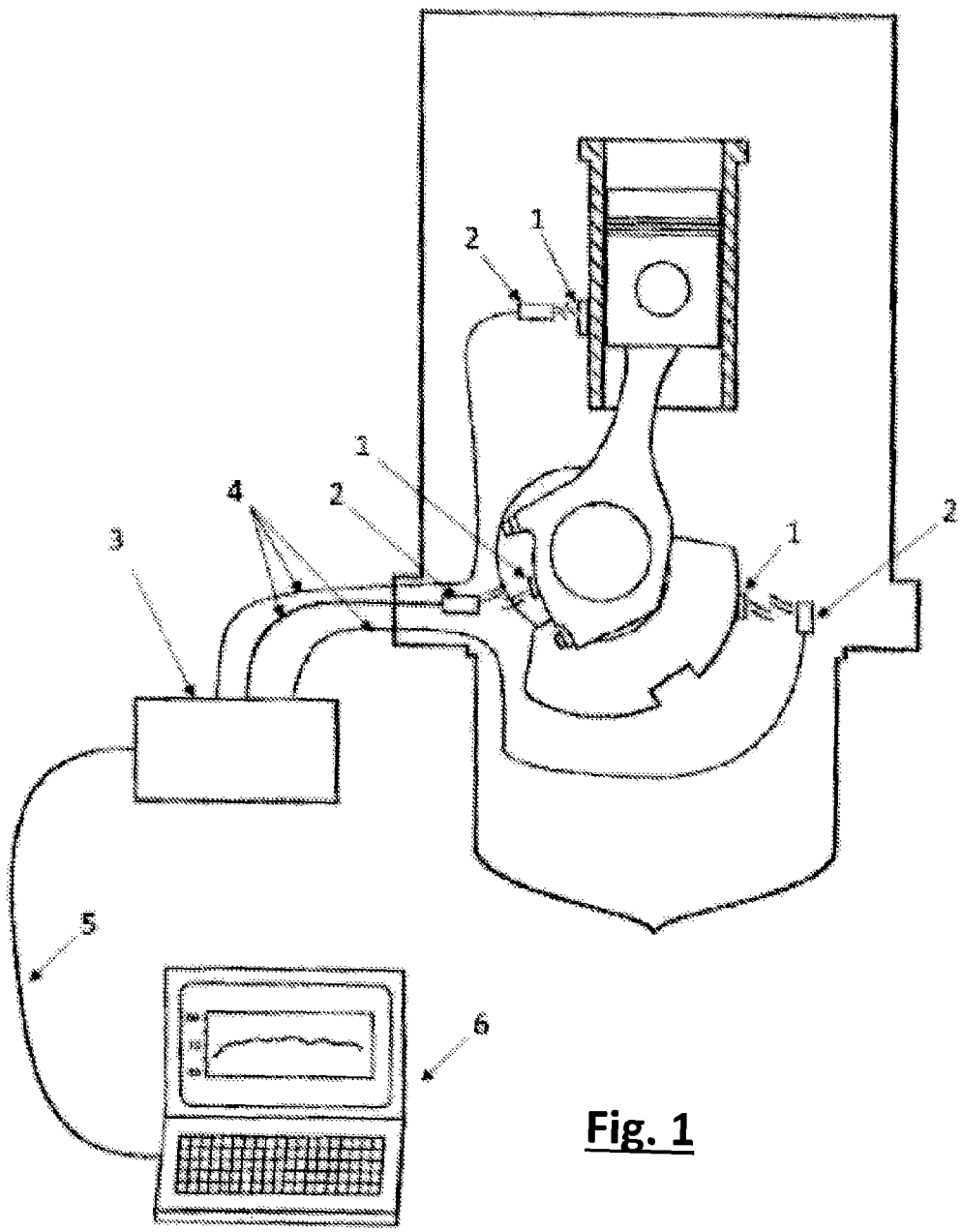
FIG. 1 shows a system for monitoring known from prior art, and in particular described in the aforementioned patent document WO 00/62029 (SENSIT)
Figure 2:
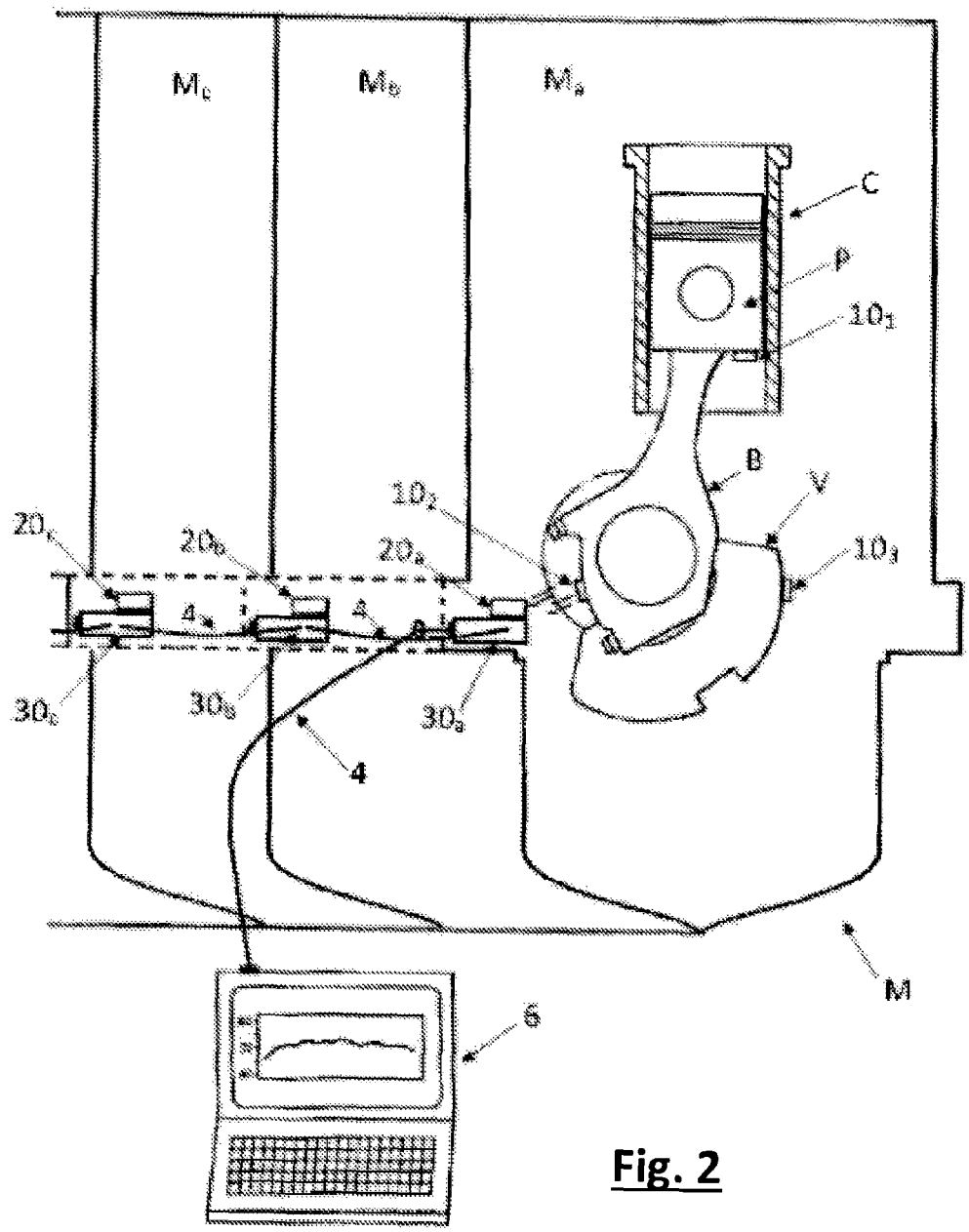
FIG. 2 shows a monitoring system in accordance with the invention arranged in one of the compartments of the engine, FIG. 3 diagrams the arrangement of a system in accordance with the invention in various compartments of a thermal engine of which the cylinders are arranged "in line", FIG. 4 diagrams the arrangement of a system in accordance with the invention in various compartments of a thermal engine of which the cylinders are arranged in a "V" shape, FIG. 5 diagrams another arrangement of a system in accordance with the invention in various compartments of a thermal engine of which the cylinders are arranged in a "V" shape

In reference to FIG. 2, the system object of the invention comprises at least one electronic control unit $30_a$, $30_b$, $30_c$. Each one of these units integrates one or several processors or microprocessors as well as a memory zone wherein are stored computer programs comprising instructions which, when they are executed by said processor or microprocessor, make it possible to perform the functionalities and steps described hereinafter, and in particular the acquisition of the various pieces of information emitted by the various sensors and/or the transmission of control information to the antenna $20_a$, $20_b$, $20_c$ to which it is connected.

In FIG. 2, the engine M comprises several compartments $M_a$, $M_b$, $M_c$. The arrangement of the system in the compartment $M_a$ shall now be described. The electronic control unit $30_a$ is connected to a single antenna $20_a$.

The latter can be directly integrated into the case of the unit $30_a$ or be offset, in which case the communication is carried out by the intermediary of a wired or wireless connection using a communication protocol known to those skilled in the art (radio waves, wifi, Bluetooth, etc.). The antenna $20_a$ used is for example a "¼ wave" antenna or PIFA (Planar Inverted-F Antenna).

Although in the systems of prior art, each antenna is generally associated with a single SAW sensor, the invention now proposes to have the antenna $20_a$ communicate with several SAW sensors $10_1$, $10_2$, $10_3$. FIG. 2 shows an embodiment wherein three SAW sensors $10_1$, $10_2$, $10_3$ are arranged in the compartment $M_a$. A lower number (for example two SAW sensors) or higher number of sensors can however be considered. The SAW sensors $10_1$, $10_2$, $10_3$ are located on parts of the engine which are in general mobile and of which the physical and/or analog parameters need to be monitored. In FIG. 2, the SAW sensors $10_1$, $10_2$, $10_3$ are positioned on a cylinder C of a thermal engine of the diesel type. A first sensor $10_1$ is positioned on the piston P, a second sensor $10_2$ on the connecting rod B and a third sensor $10_3$ on the crankshaft V. Each sensor SAW $10_1$, $10_2$, $10_3$ comprises a "mobile" antenna—since it is arranged on a part of the engine that is mobile—that is specific to it. These "mobile" antennas are configured to receive the signals emitted by the antenna $20_a$ and in order to emit, in the direction of said antenna $20_a$, response signals.

The SAW sensors $10_1$, $10_2$, $10_3$ each have a distinct resonance frequency specific to them. The unit $30_a$ integrates an emitter that simultaneously sends several electromagnetic call up signals to the antenna $20_a$, with each one of said signals having a frequency close to the resonance frequency of the SAW sensors $10_1$, $10_2$, $10_3$. The antenna $20_a$ is as such configured to emit several loops of distinct frequencies (one per SAW sensor). The signals received by then emitted by the antenna $20_a$ are transmitted to the "mobile" antennas of the SAW sensors $10_1$, $10_2$, $10_3$, then converted into surface acoustic waves that propagate on the surface of the substrates used by said SAW sensors. The properties of these surface waves, and in particular their wavelength, are modified according to the physical and/or analog parameters (temperature, pressure, stress, deformation, position in space, etc.) of the parts whereon the SAW sensors $10_1$, $10_2$, $10_3$ are arranged. These parameters more particularly affect the resonance frequency of each SAW sensor $10_1$, $10_2$, $10_3$. The latter reemit to the antenna $20_a$ a response signal at a specific resonance frequency that carries the information linked to the parameters to be monitored. In other terms, the response of the SAW sensors $10_1$, $10_2$, $10_3$ is a variation in frequency according to the parameters to be monitored, which is more advantageous than a principle based on delay lines. The response signals received by the antenna $20_a$ are then transferred to the unit $30_a$ which incorporates a suitable receiver configured to extract the information sought according to the frequencies that are actually received. The unit $30_a$ can as such call up the various SAW sensors $10_1$, $10_2$, $10_3$ by the intermediary of the single antenna $20_a$.

According to an advantageous characteristic of the invention, the antenna $20_a$ uses ISM frequencies to communicate with the sensors $10_1$, $10_2$, $10_3$. The ISM (Industrial, Scientific and Medical) bands are frequency bands of which the use for industrial, scientific, medical, domestic or similar applications, is admitted without any request for authorization with the authorities[ ]. For the European Union, the ISM frequency bands are defined in standard EN 55011 and for the USA, by the publication FCC Part 18. Using the ISM frequency bands authorizes a reading distance that can range up to 100 cm, according to the positioning of the SAW sensors $10_1$, $10_2$, $10_3$ in the engine and the geometry of the latter. Using low ISM frequencies, or close to these frequencies, i.e. between 433 MHz and 445 MHz, allows for better performance with regards to problems of reflection, diffraction and absorption of electromagnetic waves in the metal environment of the housing of the engine. Other types of frequencies suitable to those skilled in the art could however be used, in particular ISM frequencies, or close to these frequencies, between 866 MHz and 890 MHz. These higher ISM frequencies make it possible to reduce the size of the antennas, in such a way that the monitoring system object of the invention can be installed in smaller engines.

The antenna $20_a$ can also use other frequencies that are very close to the ISM frequencies. Indeed, certain SAW sensors can have frequencies that are located slightly beyond the ISM bands (from 0.5 MHz to 10 MHz for example), due to a possible "Faraday cage" effect of compartments $M_a$, $M_b$, $M_c$. In order to communicate with the sensors $10_1$, $10_2$, $10_3$ that are associated with it, the antenna $20_a$ can for example use frequencies between 423 MHz and 435 MHz and which are close to low ISM frequencies, or frequencies between 846 MHz and 870 MHz and which are close to high ISM frequencies.

Figure 3:
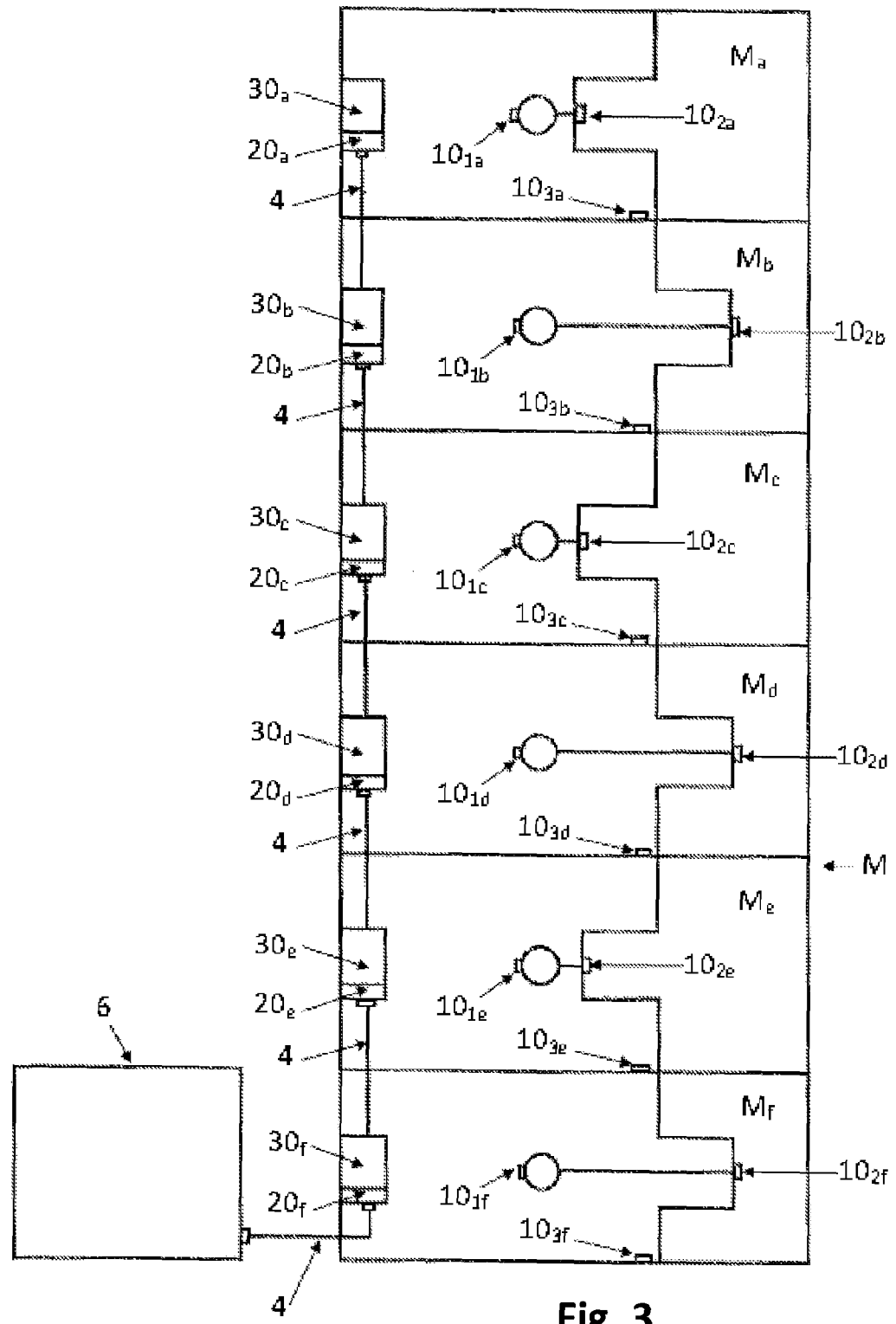
Figure 4:
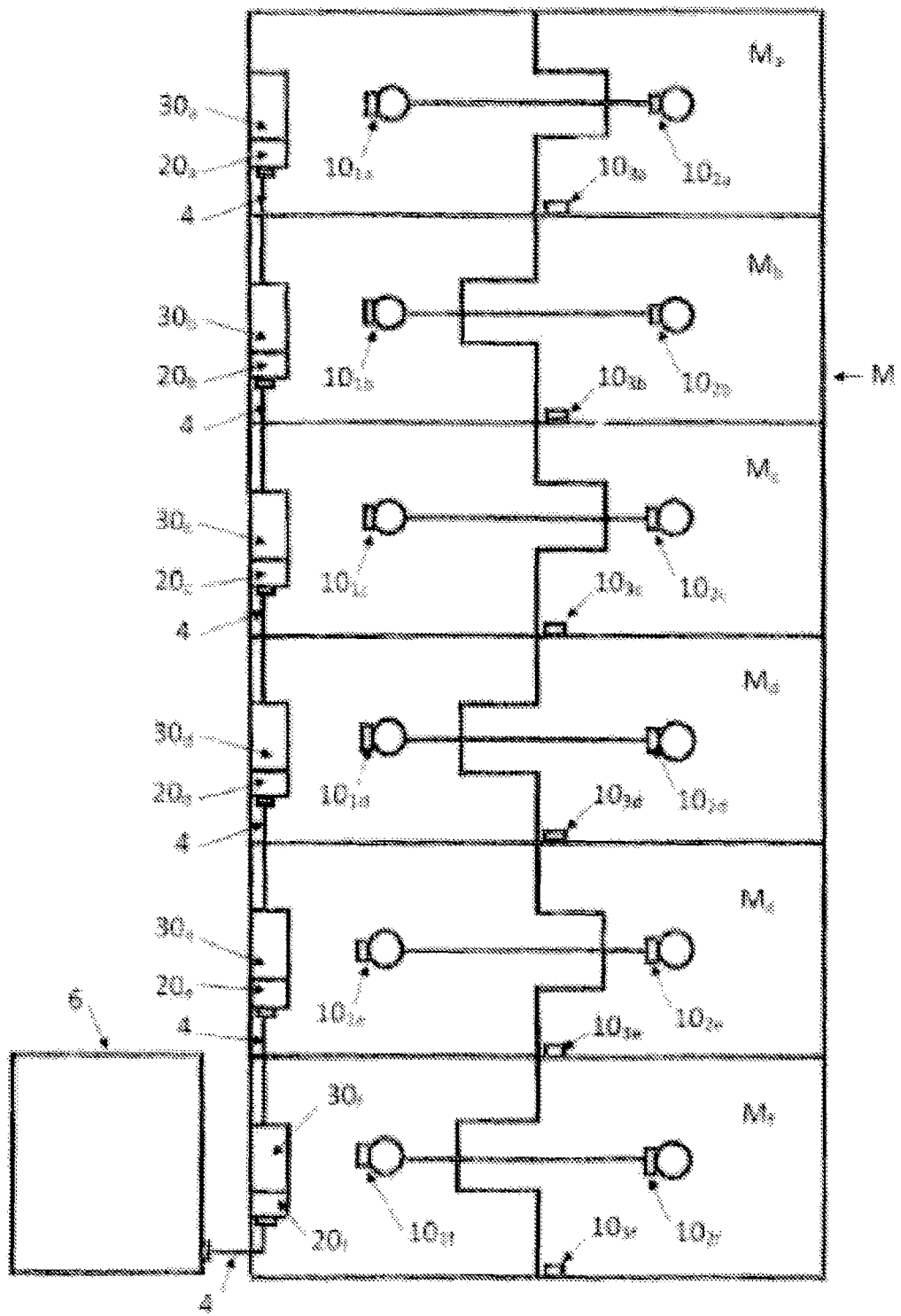
Figure 5:
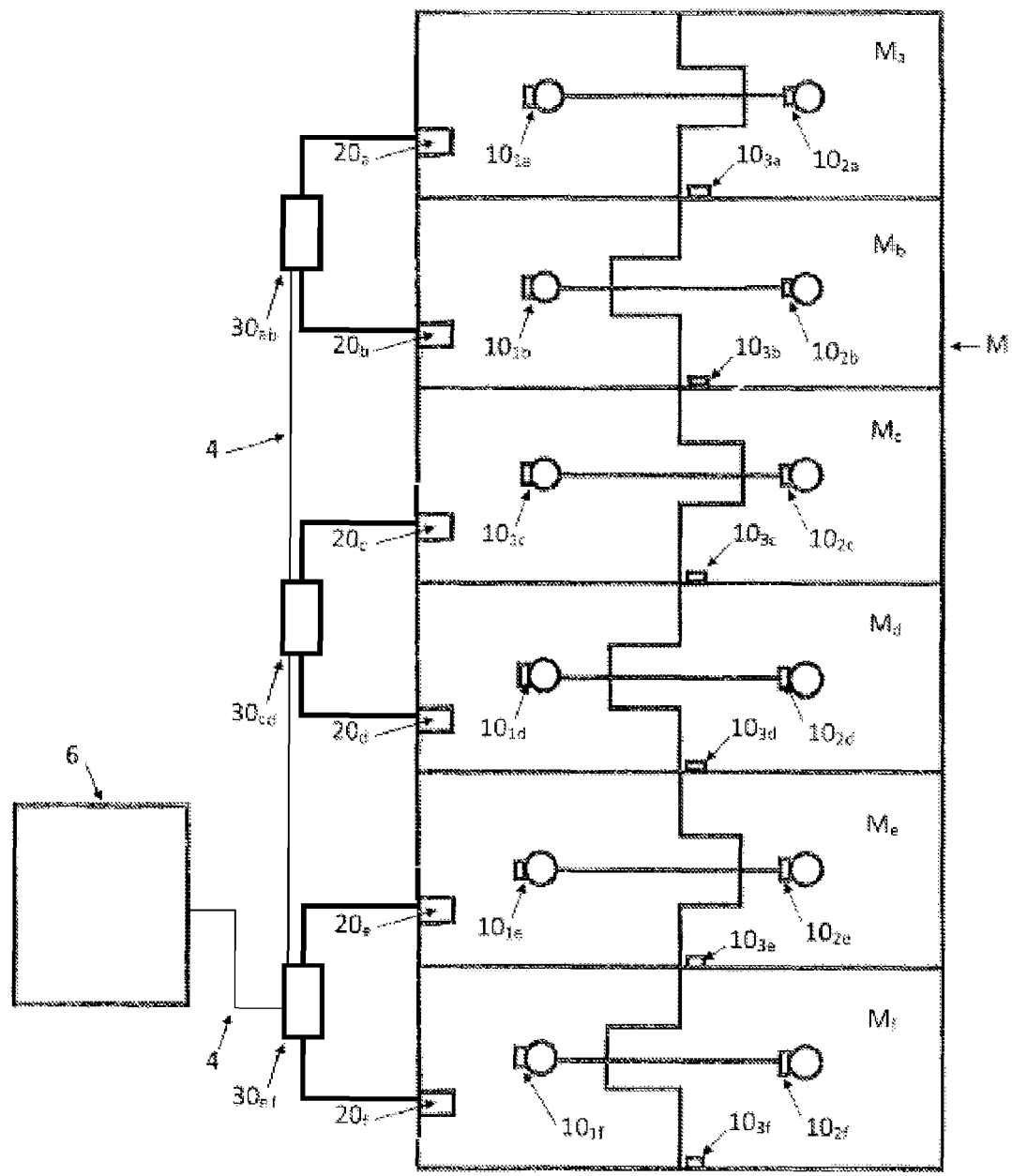

FIGS. 3, 4 and 5 show examples of uses that can be made of the system object of the invention, aiming to measure for example the temperature in the bearings and crankpins of crankshafts in an engine M of the diesel type, or of the Otto type if it is a gas engine. It is understood that other parameters such as: pressure, stress, deformation or position in space can be monitored. In FIG. 3, les cylinders of the engine are arranged "in line" while in the FIGS. 4 and 5, they are in a "V-shaped" configuration.

Each antenna $20_a, \ldots, 20_f$ is connected, alone or in pairs, to an electronic control unit $30_a, \ldots, 30_f$. In the example shown in FIGS. 3, 4 and 5, the engine M is compartmentalized. Each compartment $M_a, \ldots, M_f$ comprises: an electronic control unit $30_a, \ldots, 30f$ each one associated with a single antenna $20_a, \ldots, 20f$, (FIGS. 3 and 4) or to two (FIG. 5), each one of said antennas communicates with SAW sensors $10_{1a}, 10_{2a}, 10_{3a}, \ldots, 10_{1f}, 10_{2f}, 10_{3f}$ placed directly inside the compartments, on the parts of which the physical and/or analog parameters need to be monitored. In the case of an "in line" machine configuration (FIG. 3), there are for example SAW sensors for temperature $10_{1a}, \ldots, 10_{1f}$ on the pistons, SAW sensors for temperature $10_{2a}, \ldots, 10_f$ on the connecting rods and SAW sensors for temperature $10_{3a}, \ldots, 10_{3f}$ on the crankshaft bearings. In the case of a "V-shaped" machine configuration (FIGS. 4 and 5), there are for example SAW sensors for temperature $10_{1a}, \ldots, 10_{1f}$ on the one hand and $10_{2a}, \ldots, 10_{2f}$ on the other hand, on the connecting rods of the pairs of cylinders that are facing each other, and SAW sensors for temperature $10_{3a}, \ldots, 10_{3F}$ on the crankshaft bearings. Each part to be monitored is therefore provided with a sensor $10_{1a}, 10_{2a}, 10_{3a}, \ldots, 10_{1f}, 10_{2f}, 10_{3f}$. FIGS. 3, 4 and 5 show an embodiment wherein three SAW sensors are arranged per engine compartment. A smaller number (for example two SAW sensors) or higher number of sensors can however be considered.

The sensors $10_{1a}, 10_{2a}, 10_{3a}, \ldots, 10_{1f}, 10_{2f}$, are arranged in the various compartments $M_a, \ldots, M_f$ in such a way that sensors located in one compartment cannot communicate with an antenna connected to an electronic control unit arranged in another compartment, and more specifically in a neighboring compartment. In practice, these sensors $10_{1a}, 10_{2a}, 10_{3a}, \ldots, 10_{1f}, 10_{2f}$ are arranged in the various compartments $M_a, \ldots, M_f$ according to their resonance frequency. In order to optimize the quality of the measurements, each antenna $20_a, \ldots, 20_f$ is installed inside a compartment $M_a, \ldots, M_f$. In other terms, an antenna $20_a, \ldots, 20_f$ is installed inside each of the compartments $M_a, \ldots, M_f$. The units $30_a, \ldots, 30_f$ can each be installed outside or inside the compartments $M_a, \ldots, M_f$.

Each antenna $20_a, \ldots, 20_f$ preferentially calls up only the SAW sensors $10_{1a}, 10_{2a}, 10_{3a}, \ldots, 10_{1f}, 10_{2f}, 10_{3f}$ located in its engine compartment $M_a, \ldots, M_f$. Each antenna $20_a, \ldots, 20_f$ remains inactive with respect to the neighboring compartment or compartments due to frequencies that are different from those used in its own compartment. There is therefore no risk of interference with the other antennas installed in the other compartments and in particular the immediately neighboring compartments. More particularly, in the example shown in FIGS. 3 and 4, each unit $30_a, \ldots, 30_f$ is connected to a single antenna $20_a, \ldots, 20_f$ specific to it. Each unit (for example $30_c$) communicates simultaneously, by the intermediary of its antenna (for example $20_c$), with all of the sensors (for example $10_{1c}, 10_{2c}, 10_{3c}$) which are located in its engine compartment (for example $M_c$).

In the example shown in FIG. 5, each unit $30_{ab}, 30_{cd}, 30_{ef}$ is connected to two antennas $20_a$-$20_b$, $20_c$-$20_d$, $20_e$-$20_f$, with each one of these antennas being installed inside a compartment $M_a, \ldots, M_f$ that is dedicated to it. Each unit (for example $30_{ab}$) communicates simultaneously, by the intermediary of the pair of antennas to which it is connected (for example $20_a$-$20_b$), with all of the sensors (for example $10_{1a}, 10_{2a}, 10_{3a}$ and $10_{1b}, 10_{2b}, 10_{3b}$) which are located in the engine compartments in which said antennas are integrated (for example $M_a$ and $M_b$).

In order to prevent any harmful interference between the signals emitted by the various antennas $20_a, \ldots, 20_f$ in the engine M, a special bandwidth is allocated to each of them which allows them, for example, to emit three loops of distinct frequencies inside the same compartment $M_a, \ldots, M_f$ provided with three SAW sensors $10_{1a}, 10_{2a}, 10_{3a}, \ldots, 10_{1f}, 10_{2f}, 10_{3f}$. More particularly, in reference to the example shown in FIGS. 3 and 4, the antenna, for example $20_a$, that is connected to the unit $30_a$ arranged in the compartment $M_a$, emits frequencies in a predefined frequency band (for example 433 MHz to 439 MHz) which is different from the frequency band (for example 439 MHz to 445 MHz) in which emits the antenna $20_b$ connected to the unit $30_b$ arranged in another compartment $M_b$. The unit $30_a$ is not able as such to communicate with the sensors $10_{1b}, 10_{2b}, 10_{3b}$ which are located in the neighboring compartment $M_b$.

In the embodiment of FIG. 5, the antennas, for example $20_a$ and $20_b$, which are connected in pairs to the unit $30_{ab}$, and which are arranged respectively in the compartment $M_a$ and in the compartment $M_b$, each emit frequencies in a predefined frequency band. The unit $30_{ab}$ controls these antennas in such a way that the frequency band in which emits the antenna $20_a$ is different from the frequency band in which emits the antenna $20_b$. The unit $30_{ab}$ is as such able to communicate with the sensors $10_{1a}, 10_{2a}, 10_{3a}$ on the one hand, and $10_{1b}, 10_{2b}, 10_{3b}$ on the other hand which are located respectively in the compartments $M_a$ and $M_b$. The unit $30_{ab}$ is not however able to communicate with the sensors $10_{1c}, 10_{2c}, 10_{3c}$ which are located in the compartment $M_c$.

Preferentially, the antennas $20_a, \ldots, 20_f$ communicate with "n" SAW sensors per compartment, thanks to "2×n" pre-established distinct frequencies.

The units $30_a, \ldots, 30_f, 30_{ab}, \ldots, 30_{ef}$, are advantageously connected together by digital communication cables 4. And at least one of these units (for example $30_f$ or $30_{ef}$) is connected to monitoring equipment 6 in such a way that all of said units can communicate with this equipment. The monitoring equipment 6 is for example a computer whereon all of the information received by the various units $30_a, \ldots, 30_f, 30_{ab}, \ldots, 30_{ef}$, is viewed and/or processed and/or analyzed. The units $30_a, \ldots, 30_f, 30_{ab}, \ldots, 30_{ef}$, can also communicate with the monitoring equipment by the intermediary of digital buses that operate thanks to communication protocols such as CANopen, SAE J1939, Modbus, etc. Since on the one hand the system object of the invention comprises a single antenna per compartment and on the other hand, the electronic control units are connected together and to the monitoring equipment by a digital communication cable or a digital bus, said system reduces the constraints linked to the cabling by optimizing the space that is devoted to it, both inside and outside the engine.

The SAW sensors $10_{1a}, 10_{2a}, 10_{3a}, \ldots, 10_{1f}, 10_{2f}, 10_{3f}$, arranged in the same compartment can emit frequencies in a band of frequencies different from those emitted by the surface acoustic wave sensors arranged in another neighboring compartment. As such, any harmful interference between the signals emitted in return by SAW sensors of immediately neighboring compartments, and therefore physically close, is avoided. To do this, a specific bandwidth can be allocated to each one of the SAW sensors $10_{1a}, 10_{2a}, 10_{3a}, \ldots, 10_{1f}, 10_{2f}, 10_{3f}$ which allows them, for example, to emit in return to each one of the antennas $20_a, \ldots, 20_f$ three distinct narrow bands inside the same compartment $M_a, \ldots, M_f$ provided with three SAW sensors. In order to optimize the energy required for the operation of the installation, the bandwidth allocated to each one of the SAW sensors is preferentially narrow, for example defined over an interval (or increment) of 2 MHz. More particularly, by referring to the example shown in FIGS. 3 and 4, the sensors $10_{1a}$, $10_{2a}$, $10_{3a}$ that communicate with the antenna $20_a$ connected to the unit $30_a$, and which are arranged in the compartment $M_a$, emit in return frequencies in predefined frequency bands, respectively for example 433 MHz to 435 MHz, 435 MHz to 437 MHz, and 437 MHz to 439 MHz. These frequency bands are different from the frequency bands (for example 439 MHz to 441 MHz, 441 MHz to 443 MHz, and 443 MHz to 445 MHz) in which emit in return the sensors $10_{1b}$, $10_{2b}$, $10_{3b}$ to the antenna $20_b$ connected to the unit $30_b$, and arranged in the neighboring compartment $M_b$. The unit $30_a$ is not disturbed as such by the sensors $10_{1b}$, $10_{2b}$, $10_{3b}$ which are located in the compartment $M_b$. In this configuration, it is no longer necessary for an antenna $20_a, \ldots, 20_f$ that is installed in a compartment $M_a, \ldots, M_f$, to emit frequencies in a predefined frequency band which is different from the frequency band in which emits the antenna arranged in another compartment. Indeed, all of the antennas $20_a, \ldots, 20_f$ can each simultaneously emit several distinct frequencies covering all of the resonance frequencies of all of the sensors $10_{1a}, 10_{2a}, 10_{3a}, \ldots, 10_{1f}, 10_{2f}$, including, but not only, the frequencies close to the resonance frequencies of the sensors which are located in the compartment which is dedicated to them. All of the antennas $20_a, \ldots, 20_f$ are as such identical and dimensioned to be able to emit the same wide band frequency spectrum. It is the units $30_a, \ldots, 30_f$ which are configured to read the various frequencies in return from the sensors.

The embodiments of the invention shown hereinabove were chosen with regards to their concrete nature. It would however not be possible to list in a complete manner all of the embodiments that this invention covers. In particular, any step or means described can be replaced with an equivalent step or means, without leaving the scope of this invention.

The invention claimed is:

1. System for monitoring the physical and/or analog parameters concerning parts of an engine, said system comprising at least one electronic control unit configured to call up, by the intermediary of at least one antenna, a surface acoustic wave sensor located on one of said parts, wherein:
   the engine is compartmentalized, each compartment comprising a plurality of mobile or fixed parts of which the physical and/or analog parameters need to be monitored,
   each of these parts to be monitored is provided with a surface acoustic wave sensor, with these sensors each having a distinct resonance frequency specific to them,
   an antenna is installed inside each of the compartments, with each of these antennas being connected, alone or in pairs, to an electronic control unit,
   each antenna is controlled by the electronic control unit to which it is connected, to simultaneously emit a plurality of distinct signals having frequencies close to the resonance frequencies of the sensors which are located in the engine compartment of said antenna, so as to simultaneously communicate with all of these sensors, wherein the surface acoustic wave sensors that are arranged in the same compartment emit signals having frequencies in a band of frequencies different from those emitted by the surface acoustic wave sensors arranged in an immediately neighboring compartment, the sensors being arranged so that sensors located in one compartment cannot communicate with an antenna located in an immediately neighboring compartment.

2. System according to claim 1, wherein the antenna which is installed in a compartment, emits signals having frequencies in a predefined frequency band which is different from the frequency band in which emits the antenna arranged in another compartment, so that each antenna calls up only the surface acoustic wave sensors located in its compartment.

3. System according to claim 1, wherein the surface acoustic wave sensors arranged in the same compartment, each emit signals having frequencies in a narrow frequency band, defined over an interval of 2 MHz.

4. System according to claim 1, wherein each electronic control unit is connected to a single antenna specific to it.

5. System according to claim 1, wherein each electronic control unit is connected to two antennas, with each one of these antennas being installed inside a compartment that is devoted to it.

6. System according to claim 1, wherein each surface acoustic wave sensor comprises an antenna specific to it.

7. System according to claim 1, wherein each surface acoustic wave sensor is installed on a part that is mobile.

8. System according to claim 1, wherein the sensors are arranged in the various compartments in such a way that sensors located in one compartment cannot communicate with an antenna installed in another compartment.

9. System according to claim 1, wherein the electronic control units are each installed outside or inside the compartment.

10. System according to claim 1, wherein the electronic control units are connected together by digital communication cables, at least one of said units being connected to monitoring equipment in such a way that all of said units can communicate with said equipment.

11. System according to claim 1, wherein the electronic control units communicate with monitoring equipment by the intermediary of a digital bus.

12. System according to claim 1, wherein each antenna uses ISM frequencies to communicate with the sensors that are associated with them.

13. System according to claim 12 wherein each antenna uses ISM frequencies between 433 MHz and 445 MHz.

14. System according to claim 12, wherein each antenna uses ISM frequencies between 866 MHz and 890 MHz.

15. System according to claim 1, wherein each antenna uses frequencies between 423 MHz and 435 MHz, to communicate with the sensors that are associated to them.

16. System according to claim 1, wherein each antenna uses frequencies between 846 MHz and 870 MHz, to communicate with the sensors that are associated to them.

17. System according to claim 1, wherein each antenna used is a "¼ wave" antenna or PIFA.

18. Method for monitoring the physical and/or analog parameters concerning the parts of an engine, by calling up, by the intermediary of at least one antenna, a surface acoustic wave sensor located on one of said parts, comprising:
   compartmentalizing the engine in such a way that each compartment comprises a plurality of parts of which the physical and/or analog parameters need to be monitored,
   arranging on each of these parts to be monitored, a surface acoustic wave sensor, these sensors each having a distinct resonance frequency specific to them,
   installing an antenna inside each compartment, connecting each one of these antennas, alone or in pairs, to an electronic control unit, calling up each sensor by simultaneously emitting, from each antenna, a plurality of distinct signals having frequencies close to the resonance frequencies of the sensors which are located in the engine compartment of said antenna, so as to simultaneously communicate with all of these sensors, arranging the surface acoustic wave sensors in the same compartment, so as to emit signals having frequencies in a band of frequencies different from those emitted by the surface acoustic wave sensors arranged in an immediately neighboring compartment, arranging the sensors so that sensors located in one compartment cannot communicated with an antenna located in an immediately neighboring compartment.

* * * * *